(12) United States Patent
Miola

(10) Patent No.: US 6,267,289 B1
(45) Date of Patent: *Jul. 31, 2001

(54) SAFETY PROCESS FOR PRESSURE EQUIPMENT IN CONTACT WITH CORROSIVE FLUIDS

(75) Inventor: Cesare Miola, Sannazzaro (IT)

(73) Assignee: Snamprogetti S.p.A., San Donato Milanese (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/142,163
(22) PCT Filed: Mar. 21, 1997
(86) PCT No.: PCT/EP97/01202
 § 371 Date: Sep. 21, 1998
 § 102(e) Date: Sep. 21, 1998
(87) PCT Pub. No.: WO97/34690
 PCT Pub. Date: Sep. 25, 1997

(30) Foreign Application Priority Data

Mar. 21, 1996 (IT) ............................................. M196A0558

(51) Int. Cl.$^7$ ............................ B23K 31/00; B23K 31/02
(52) U.S. Cl. ....................... 228/119; 228/175; 228/184; 422/241; 220/3
(58) Field of Search ................................. 228/119, 175, 228/184; 220/3; 422/241

(56) References Cited

U.S. PATENT DOCUMENTS

| | | | |
|---|---|---|---|
| 2,253,093 | * | 8/1941 | Raichle et al. ............................ 220/3 |
| 2,365,696 | * | 12/1944 | Grubb ................................. 29/148.2 |
| 3,704,509 | * | 12/1972 | Yamauchi ............................ 29/471.1 |
| 4,032,243 | * | 6/1977 | Keifert et al. ......................... 403/272 |
| 4,072,787 | * | 2/1978 | Ricks .................................... 428/594 |
| 4,117,201 | * | 9/1978 | Keifert ................................ 428/591 |
| 4,235,361 | * | 11/1980 | Hays et al. ............................ 228/173 |
| 4,244,482 | * | 1/1981 | Baumgart et al. ........................ 220/3 |
| 4,252,244 | * | 2/1981 | Christian et al. ......................... 220/3 |
| 4,266,712 | * | 5/1981 | Park et al. ............................ 228/175 |
| 4,291,104 | * | 9/1981 | Keifert ................................ 428/594 |
| 4,818,629 | * | 4/1989 | Jenstrom et al. ..................... 428/594 |
| 5,150,831 | * | 9/1992 | Jordan et al. ......................... 228/184 |
| 5,305,946 | * | 4/1994 | Heilmann ............................ 228/184 |
| 6,010,669 | * | 1/2000 | Miola et al. .......................... 422/241 |

FOREIGN PATENT DOCUMENTS 56-017628 * 2/1981 (JP) ...................................... 228/175

* cited by examiner

Primary Examiner—Tom Dunn
Assistant Examiner—L. E Edmondson
(74) Attorney, Agent, or Firm—Oblon, Spivak, McClelland, Maier & Neustadt, P.C.

(57) ABSTRACT

Method for the safety and extension of the operating life of pressure equipment having an internal chamber suitable for containing a process fluid, surrounded by a pressure-resistant body (1) equipped with weep-holes (2), made of a material subject to corrosion by contact with said process fluid operation, coated inside with an anticorrosive lining (4) made up of several elements welded to each other, wherein said lining weldings (3) are completely isolated from contact with the process fluid of the normal operating run, by a coating with adjoining strips (or plates) (10, 10', 10", 10'''), of the same material as said lining (4) or other corrosion-resistant material weldable thereto, which are subsequently seal-welded on the edges to said lining (4) and to each other, characterized in that the arrangement and welding of the edges of these strips (10, 10', 10", 10''') are such to create a network of underlying interstices (or meati) (9,11), communicating with each other and at least one weep-hole.

22 Claims, 6 Drawing Sheets

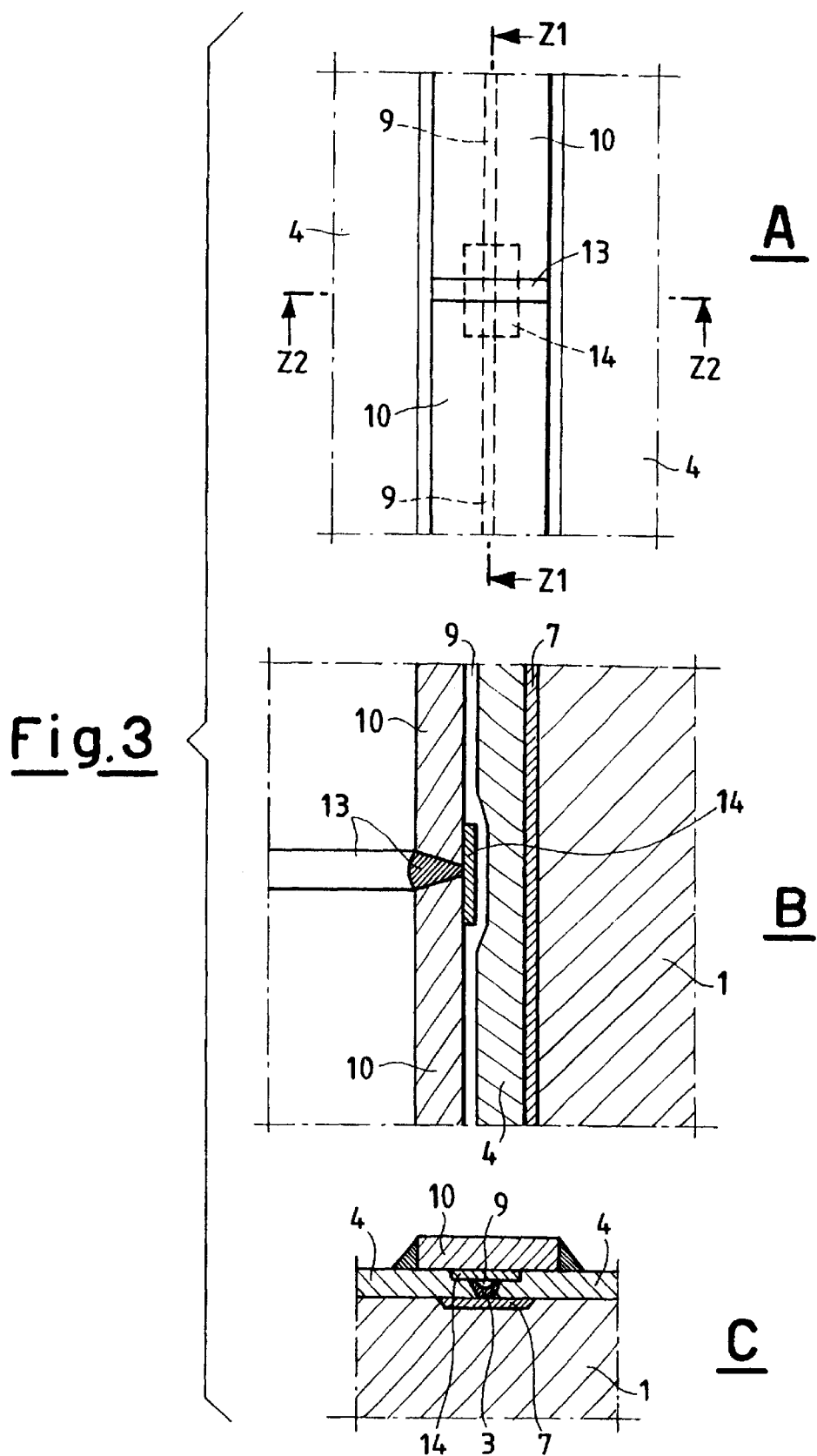

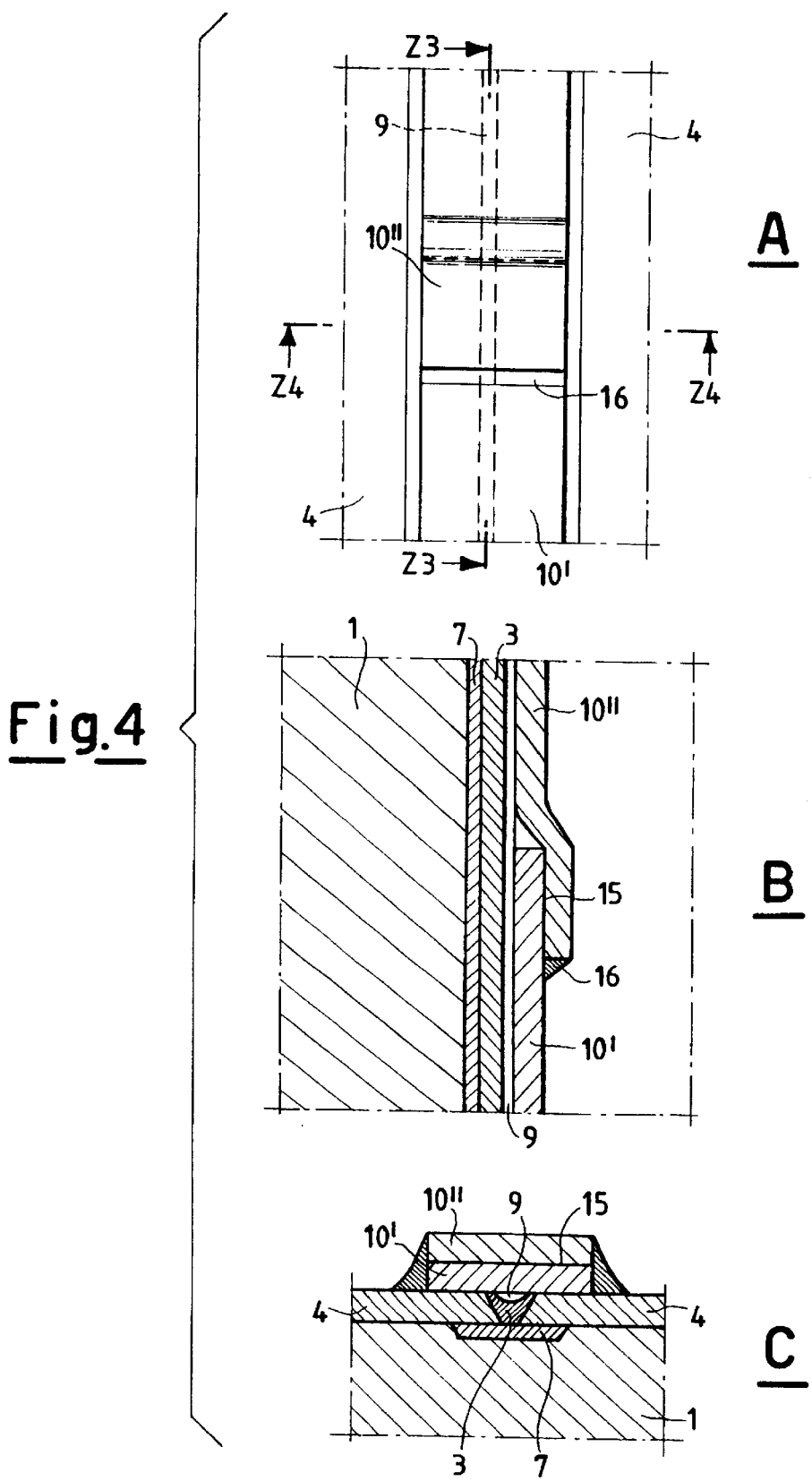

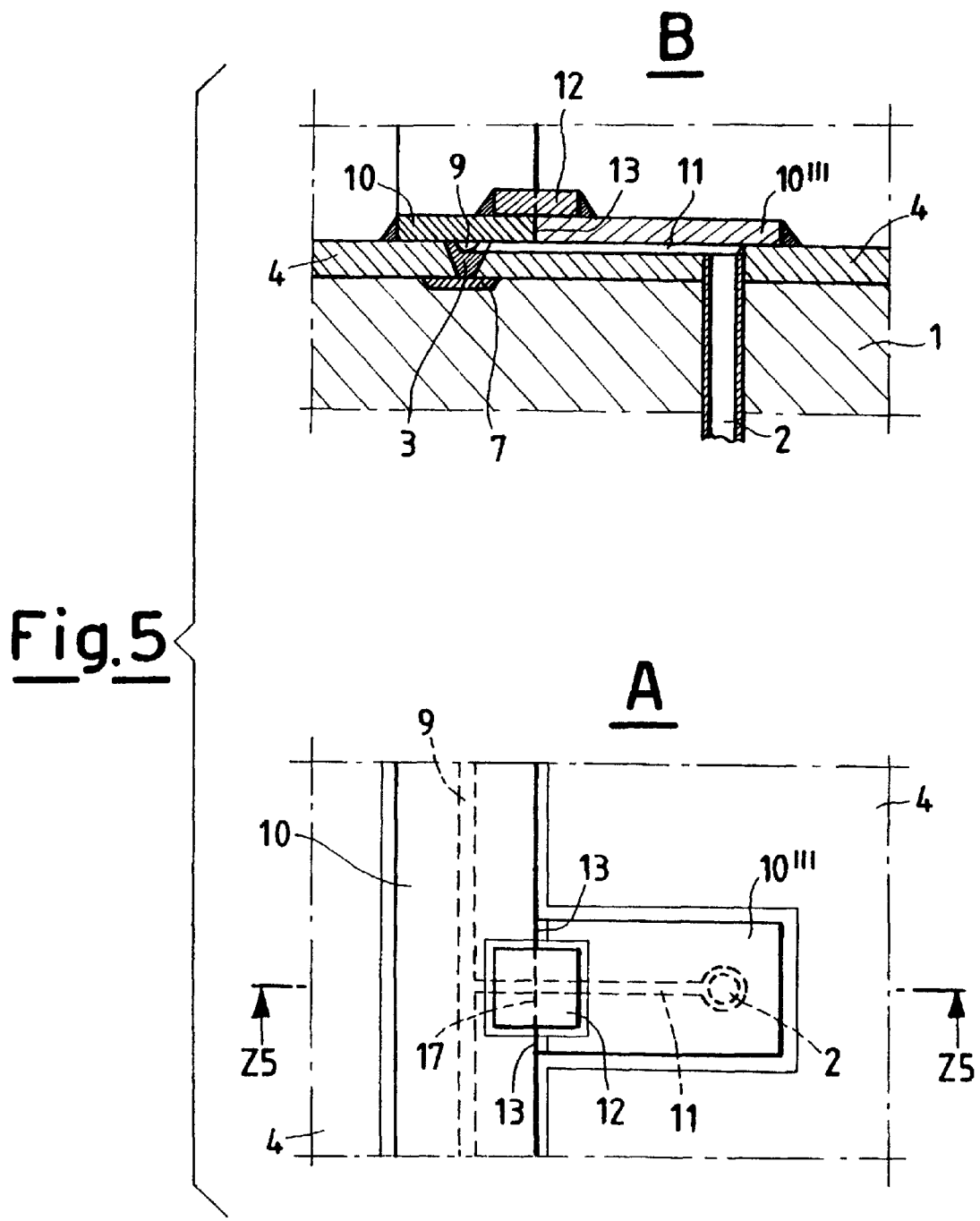

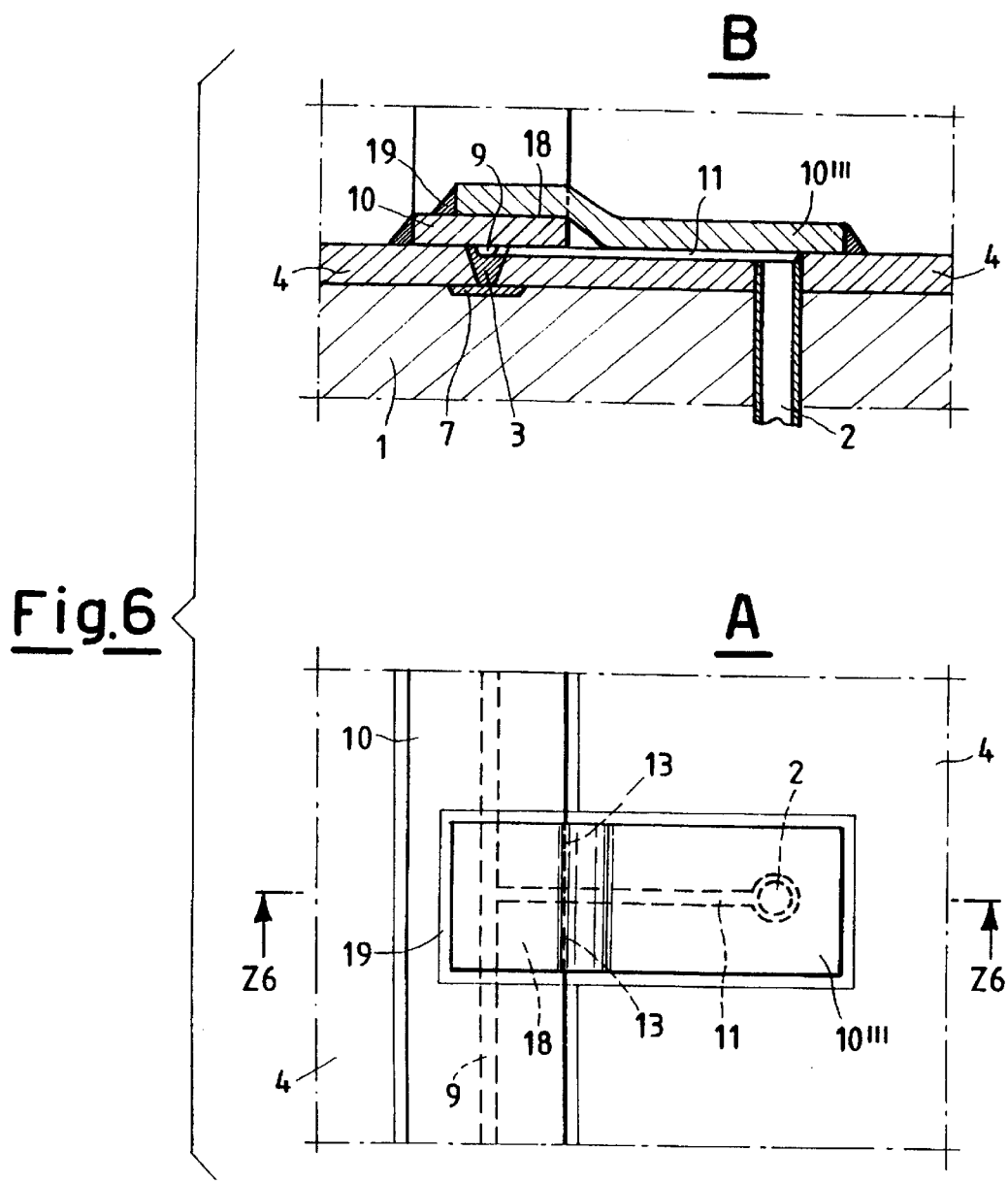

SAFETY PROCESS FOR PRESSURE EQUIPMENT IN CONTACT WITH CORROSIVE FLUIDS

Figure 1:
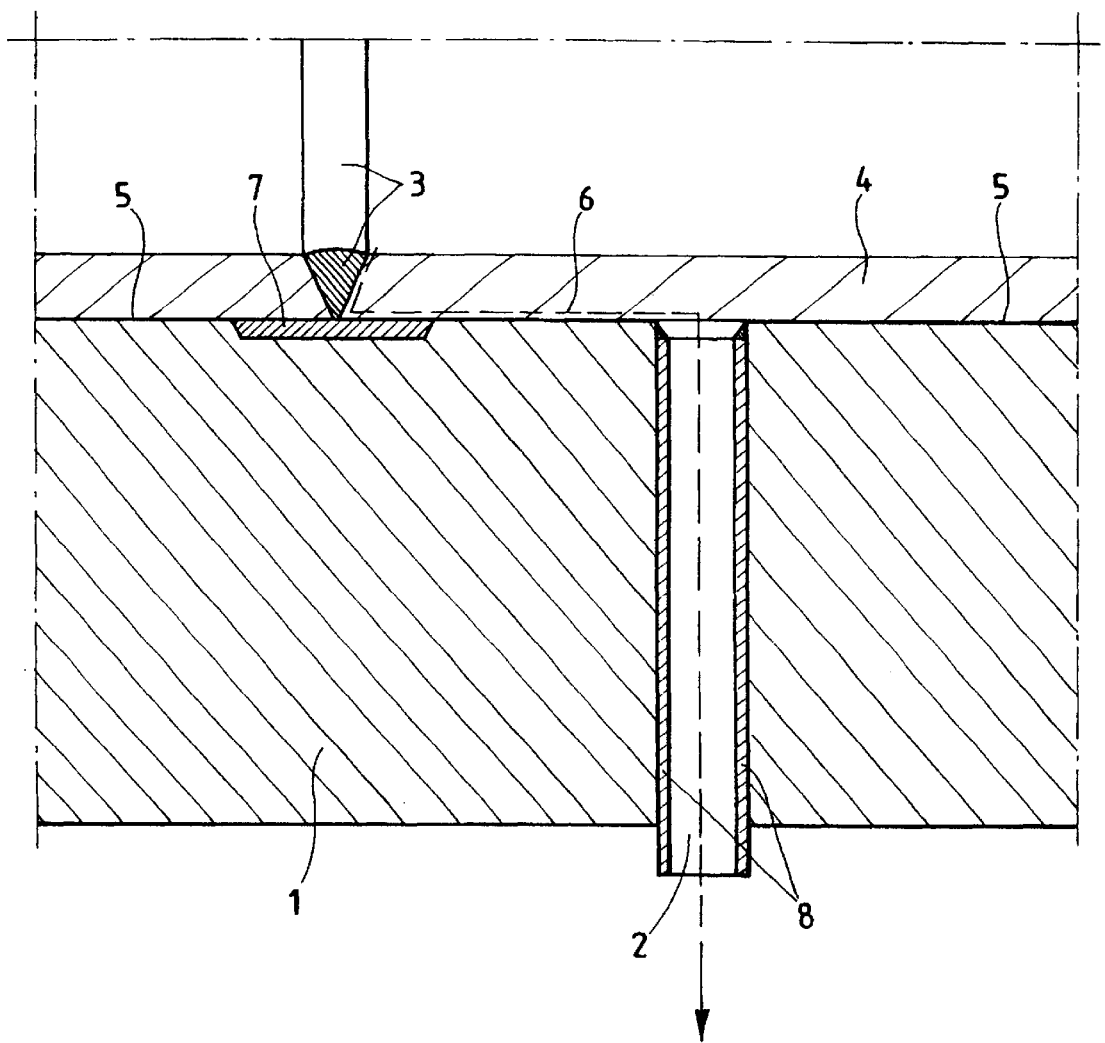

The present invention relates to a method for the safety of pressure equipment in contact with corrosive fluids and to the modified equipment thus obtained.

More specifically, the present invention relates to a method for the safety of equipment normally operating under pressure, which is in contact with corrosive fluids and therefore comprises anticorrosive lining overlying the sealing structure (pressure-resistant body).

Typical equipment of this kind is that which is present in many industrial chemical plants, such as, for example, reactors, heat-exchangers, condensers and evaporators, whose operating conditions comprise pressures of between 50 and 1000 bars and temperatures of between 100 and 500° C., in contact with acid, basic or generally saline fluids having high corrosive potential especially with respect to carbon or low-alloy steel which is the material normally selected for the sealing of equipment.

Typical processes which require the use of high pressure equipment in contact with corrosive fluids are, for example, those for the production of urea by direct synthesis starting from ammonia and carbon dioxide. In these processes, ammonia generally in excess and carbon dioxide are reacted in one or more reactors, at pressures usually of between 100 and 250 bars and temperatures of between 150 and 240° C., obtaining a mixture at the outlet consisting of a water solution of urea, ammonium carbamate not transformed into urea and the excess ammonia used in the synthesis. The reaction mixture is purified of the ammonium carbamate contained therein by its decomposition in decomposers operating, in succession, at gradually decreasing pressures. In most of the existing processes, the first of these decomposers operates at pressures which are basically equal to the synthesis pressure or slightly lower, and normally uses "stripping" agents to decompose the ammonium carbamate with the contemporaneous removal of the decomposition products. The "stripping" agents can be inert gases, or ammonia or carbon dioxide, or mixtures of inert gases with ammonia and/or carbon dioxide, the "stripping" also being possible by using the excess ammonia dissolved in the mixture coming from the reactor (auto-stripping) without supplying therefore any external agent.

The decomposition products of ammonium carbamate ($NH_3$ and $CO_2$) together with the possible "stripping" agents, excluding inert gases, are normally condensed in suitable condensers obtaining a liquid mixture comprising water, ammonia and ammonium carbamate, which is recycled to the synthesis reactor. In plants which are technologically more advanced, at least one condensation step is carried out at pressures which are basically equal to or slightly lower than those of the reactor.

As a reference, it is possible to cite, among the many existing ones, patents U.S. Pat. Nos. 3,886,210, 4,314,077, 4,137,262, and published European patent application 504.966, which describe processes for the production of urea with the above characteristics. A wide range of processes mainly used for the production of urea is provided in "Encyclopedia of Chemical Technology", 3° Edition (1983), Vol.23, pages 548–574, John Wiley & Sons Ed.

The most critical steps in the process are those in which the ammonium carbamate is at its highest concentration and highest temperature, and therefore in the above processes, these steps coincide with the reactor and subsequent equipment for the decomposition (or stripping) and condensation of the ammonium carbamate operating under analogous or similar conditions to those of the reactor. The problem to be solved in this equipment is that of the corrosion and/or erosion caused by the ammonium carbamate, ammonia and carbon dioxide which act as highly corrosive agents, especially in the presence of water, at the high temperatures and pressures necessary for the synthesis of urea.

Various solutions to the problems of corrosion of the type described above have been proposed, many of which have been applied in existing industrial plants. Numerous metals and alloys are in fact known which are capable of resisting for sufficiently long periods, in various cases, to potentially corrosive conditions which are created inside industrial chemical equipment. Among these lead, titanium, zirconium, tantalum and several stainless steels such as, for example, AISI 316L (urea grade), INOX 25/22/2 Cr/Ni/Mo steel, austenitic-ferritic steels, etc., can be mentioned. However, for economic reasons, the above type of equipment is not normally entirely constructed with these corrosion-resistant alloys or metals. Usually hollow bodies, containers or columns are produced in normal carbon or low-alloy steel, possibly with several layers, having a thickness varying from 20 to 400 mm, depending on the geometry and the pressure to be sustained (pressure-resistant body), whose surface in contact with the corrosive or erosive fluids is uniformly covered with an anticorrosive metal lining from 2 to 30 mm thick.

In the above plant equipment or units, the anti-corrosive lining is produced by the assembly and welding of numerous elements appropriately shaped to adhere as much as possible to the form of the pressure-resistant body, in order to create, at the end, a structure hermetically-sealed against the high operating pressure. The different junctions and weldings carried out for this purpose frequently require the use of particular techniques depending on the geometry and nature of the parts to be joined.

Whereas stainless steel can be welded to the underlying "pressure-resistant body" made of carbon steel, but has a higher thermal expansion coefficient which favours, during operation, the creation of fractures along the welding line, titanium cannot be welded to steel and in any case has analogous fracture problems in the weldings as it has an expansion coefficient which is much lower than carbon steel.

For this reason resort is made to techniques which often require complex equipment and operating procedures. In certain cases the lining is effected by welding deposit instead of plates welded to each other and onto the pressure-resistant body. In other cases, especially with materials which cannot be welded to each other, it is necessary to "explode" the lining onto the pressure-resistant body to be sure of obtaining a satisfactory support.

A certain number of "weep-holes" are however applied to all the above equipment for the detection of possible losses of anticorrosion lining.

A weep-hole normally consists of a small pipe 5–30 mm in diameter made of a material which is resistant to corrosion and is inserted in the pressure-resistant body until it reaches the contact point between the latter and the lining in corrosion-resistant alloy or metal. If there is a loss of lining, owing to the high pressure, the internal fluid, which is corrosive, immediately spreads to the interstitial area between the lining and the pressure-resistant body and, if not detected, causes rapid corrosion of the carbon steel of which the latter is made. The presence of weep-holes enables these losses to be detected. For this purpose all interstitial areas underneath the anticorrosion lining must communicate with at least one weep-hole. The number of weep-holes is usually from 2 to 4 for each ferrule, therefore, for example, in a reactor of average dimensions, having a surface expansion of about 100 m², there are normally about 20 weep-holes.

The above equipment also has, normally in the upper part, at least one circular opening, called "man-hole", which allows access to operators and equipment for inspections and minor internal repairs. These 10 openings usually have diameters of between 45 and 60 cm and at the most allow the passage of objects having a section within these dimensions.

In spite of the above measures, it is generally known that the welding lines and points of the protective "lining" form a weak point in the structure of chemical equipment. In fact microfractures can be found during operation for the above reasons of different thermal expansion between the materials of the pressure-resistant body and anticorrosive lining, and also preferential corrosions on the weldings or surrounding areas, owing to imperfections in the structure of the metal and to differences in the electrochemical potential between the welded metals. A loss of protective lining therefore most probably occurs near its welding points. On the other hand there is no possibility in practice of applying a monoblock lining.

As already mentioned, in the case of a loss, the fluid flows out of the lining and floods the interstices or meati or void channels present between the lining and pressure-resistant body. In these cases the loss is normally detected through the weep-hole, but corrosion may occur however, even extensively, in the underlying carbon steel, before the loss is noticed. In the most serious cases which have led to serious corrosion and explosion of the equipment, the out-flowing fluid, for example a concentrated solution of ammonium carbamate in a synthesis plant of urea, can form semisolid mixtures together with the corrosion residues, blocking the vents towards the weep-holes, thus preventing the loss itself to be detected. In the site of the loss, which can no longer be revealed, the corrosive fluid continues its action on the pressure-resistant body, deeply corroding the structure, making it unusable, or even worse, causing the equipment to explode.

In order to avoid these phenomena, numerous solutions have been proposed, such as, for example, in German patent DE 2.052.929, according to which a cover is made with a double lining interrupted by communication channels, thus incurring a considerable increase in the production costs of the equipment, and without providing a satisfactory solution to the problem of the contact of the pressure-resistant body with the process fluid in the case of a possible loss.

In practice, however, most of the existing chemical plants, especially those not of recent construction, have a simple lining with circular and longitudinal weldings, in which the only safety element for detecting losses is represented by weep-holes. For the safety regulations presently required, this solution is completely unsatisfactory and there is a strong demand in the field for increasing both the average operating life and the capacity and rapidity of detecting possible losses (with a consequent increase in security) of the chemical equipment in contact with corrosive substances.

The Applicant has now found a satisfactory and advantageous solution to the above drawbacks with a simple and innovative approach which allows an increase in the duration and reliability of pressure equipment comprising a pressure-resistant body consisting of a material subject to corrosion by contact with the process fluid, and an internal anticorrosive lining in contact with said fluid, even when this equipment is already operating in the plant. Particularly in the latter case, the safety process can be carried out without removing the equipment from the plant and using the man-hole as the only operative access to the inside of the equipment.

The present invention therefore relates to pressure equipment comprising an internal chamber suitable for containing a process fluid, surrounded by a pressure-resistant body equipped with weep-holes, consisting of a material subject to corrosion by contact with said process fluid during operation, coated inside with an anticorrosive lining made up of several elements welded to each other, a method for avoiding contact of said pressure-resistant body with the process fluid as a result of a possible loss from the weldings, and consequently increasing the safety of said pressure equipment, comprising the following steps:

*a*) extension of at least a part of the weep-holes through the lining so as to form an outlet in the internal surface of the equipment;

*b*) covering the weldings with adjoining strips (or plates) of the same material as the lining or other corrosion-resistant material weldable thereto, previously shaped to suitably lay on the surface of the lining near the weldings;

*c*) placing further strips of the same material as the lining, or other corrosion-resistant material weldable thereto, each adjoining to at least one of the above strips of step (b), until all the outlets of the weep-holes are covered;

*d*) hermetically welding the edges of each strip of steps (b) and (c) onto the lining and edges of other adjoining strips, to obtain, between each of these strips and the underlying surface of the lining and/or its weldings, a hermetic interstitial area (or meati) with respect to the internal chamber and suitable for the flow of the process fluid;

characterized in that:

the arrangement and weldings between the edges of at least a part of the adjoining strips, are effected so that, beneath each of the weldings between the adjoining edges, there is an opening between the existing interstitial areas (or meati) on each side of the welding, these openings being hermetic with respect to the internal chamber and in such a quantity and so arranged as to put each interstitial area (or meatus), or part of it, in communication with at least one of the weep-hole outlets.

According to the above method, the different overlying elements are so arranged as to form the internal wall of the equipment, so that, in case of a loss at a point near the welding in contact with the process fluid, the fluid itself, before reaching one of the weep-holes appropriately extended towards the lining (normally corresponding to those already existing before the safety intervention), enters in contact only with the surfaces of a corrosion-resistant material, thus avoiding any possible damage of the pressure-resistant body. At the same time, the arrangement of the different parts inside the equipment and the presence of meati passing between the weldings of two adjoining covering strips, ensures the rapid detection of the fluid flowing out of a possible loss, using the same weep-holes existing before the intervention of the present invention. It is therefore possible to rapidly detect a possible loss during operation from a welding of the lining complex, and at the same time maintaining the integrity of the pre-existing structure as it is not normally necessary to apply other weep-holes, and avoiding any contact of the pressure-resistant body with the process fluids at the moment of a possible loss.

The application, during the embodiment of the method, of one or more weep-holes in addition to those already existing is not, however, excluded from the scope of the present invention, especially when particular geometries and arrangements of the elements make it necessary (for example near the outlets), provided the number is limited, normally less than 30%, preferably less than 10% than the original ones.

A further object of the present invention relates to equipment obtained by the embodiment of the above method. In this equipment the original weldings of the lining are not in contact with the process fluid during operation, as they are covered, hermetically, by the above strips (or plates) of corrosion-resistant material. The risk is thus avoided of a prolonged action of the process fluid on these weldings causing their perforation, by local corrosion or erosion, with the consequent disastrous effects of an outflow of the fluid in direct contact with the easily corrodible material of the pressure-resistant body. In the case of a possible loss of one of the weldings subsequently effected on the edges of the covering strips to ensure the hermetic sealing of the underlying interstices (or meati), the process fluid is directed into these until it reaches the nearest outlet of a weep-hole, but it has no corrosive effect, at least in the relatively rapid times necessary for detecting the loss, on the surfaces of the materials with which it is in contact, as these materials, in accordance with the present invention, are all resistant to corrosion.

As previously specified, the method of the present invention can be particularly applied to the high or medium pressure section of a plant for the synthesis of urea. These can be basically identified in synthesis reactors of urea, equipment for the decomposition of non-transformed carbamate and containers for the condensation of $NH_3$ and $CO_2$ with the formation of carbamate solutions.

The term "adjoining strips (or plates)" as used in the present invention and claims, refers to two or more strips, each of which has at least a part of the edge adjacent to or in contact with at least a part of the other. The term "adjoining edges" refers to these edges of strips adjoining, adjacent to or in contact with each other.

The term "communication", as used in the present description and in the claims, should be considered as referring to the behaviour of a fluid, for which two points (or areas) are communicating if a fluid, particularly the process fluid, can flow from one to the other. The term "original", as used hereafter with reference to the elements of equipment such as weldings, lining, weep-holes, etc., identifies those elements already present in the equipment before the application of the method of the present invention.

The equipment to which the method of the present invention is applicable can be any known pressure equipment in contact with potentially corrosive fluids during operation. This equipment normally comprises a steel pressure-resistant body capable of resisting even very high operating pressures (up to 1000 bars and over, preferably between 100 and 500 bars), but subject to corrosion if placed directly in contact with process fluids. This, depending on project requirements, can have several layers or a single wall, possibly subjected to annealing. In the internal chamber, in contact with the process fluid there is a lining in a corrosion-resistant material, which is usually a metal selected from stainless steel, special austenitic-ferritic steels, lead, titanium, zirconium, vanadium, tantalum or one of their alloys. The lining can be welded to the pressure-resistant body, or, in many cases, just fitted onto it. The lining is produced, according to the known art, by welding plates (or ferrules) of the metal selected to each other, until the internal surface of the pressure-resistant body is completely covered, as well as the parts inside the outlets and man-hole which normally form part of the equipment. The weldings of the lining are normally fitted onto strips of the same material as the lining, preferably inserted into a groove mechanically applied to the pressure-resistant body. As previously mentioned, there are numerous weep-holes in the pressure-resistant body, for the purpose of controlling possible losses of lining during operation. A detail of the arrangement of the elements in equipment of the type specified above is schematically represented in FIG. 1 enclosed, relating to a section comprising a welding of the lining and a weep-hole.

According to the method of the present invention, in step (a) at least a part of the existing weep-holes are extended towards the lining, by drilling or any other known technique, until it reaches the internal surface. Each weep-hole comprises an internal lining of anti-corrosive material, which is also extended and welded onto the edges around the outlet thus produced. Each outlet thus forms an opening in the lining, preferably having a diameter of between 5 and 30 mm. It is not necessary to extend all the existing weep-holes, but only a sufficient number to guarantee easy communication with all the interstitial areas (or meati) produced in the subsequent steps of the present method. The number of weep-holes actually extended can be evaluated by the expert in the field, and is normally between 70 and 100% of those existing, depending on the dimensions and geometry of the equipment and the surface density of the holes themselves.

The application, during the embodiment of the method, of one or more weep-holes in addition to those already existing is not, however, excluded from the scope of the present invention, especially when particular geometries and arrangements of the elements make it necessary (for example near the outlets, provided the number is limited, normally less than 30%, preferably less than 10% than the original ones.

In step (b) of the method of the present invention, the weldings of the lining are covered by suitably shaped strips (or plates), resistant to corrosion under the operating conditions of the equipment. In most cases and particularly in plants for the production of urea, the chemical equipment has cylindrical, or curved sections. The above strips should therefore be appropriately curved or shaped to adapt themselves to the surface to be covered. However as they are easily deformed, the suitable curvature can be obtained with normal instruments available to experts in the field.

The strips are arranged adjacently one after the other on all the weldings so as to form, after application, a regular surface without gaps. It is preferable to use strips having a width of between 50 and 300 mm, and a length varying from a few centimetres to several meters, depending on the requirements. The length and shape of the strips however are preferably selected to as allow easy access inside the equipment through the man-hole. Strip thicknesses of between 2 and 30 mm are preferably used, selected on the basis of the potential corrosive and/or erosive action of the process fluid.

Two adjoining strips can be arranged in various ways according to the present invention, provided this allows: a hermetic welding system of the edges of the strips, which isolates the underlying weldings of the lining from the process fluid during normal operation (according to step (d) below), and suitable communication for the flow of a fluid between the interstitial areas present under each of the two adjoining strips. The strips will normally be consecutive, i.e. joined one after another by the transversal edges, or strips perpendicular to each other, in which a transversal edge is joined to a longitudinal edge (parallel to the covered welding). In the junctions between two adjoining strips, different measures can be carried out, all included in the scope of the present invention. It is possible, for example, to put a short part of the edge of one of the strips over the edge of the other, giving the former an "S" shape. Or the two adjoining edges can be placed next to each other; or again, a metal plate can be placed under two adjoining edges adjacent in the junction area, possibly forming a cavity in the underlying lining (and welding), suitable for containing a plate, to improve the support of these adjoining edges.

According to the present invention, the covering strips consist of the same metal as the original lining, or a metal or alloy weldable thereto. This can be selected each time from materials known to be corrosion-resistant under the operating conditions of the equipment. This metal or metal alloy is preferably selected from titanium, zirconium, or their alloys, or particularly, from stainless steels such as, for example, AISI 316L steel (urea grade), INOX 25/22/2 Cr/Ni/Mo steel, special austenitic-ferritic steels, etc. The selection of a metal which has a higher resistance to corrosion (however measured) than that of the original lining is left to the expert in the field.

The covering strips of the weldings can be fixed, before being welded in turn, with the normal methods available to experts in field, provided these are compatible with the operating conditions of the equipment. Mechanical fixings or welding points can normally be used.

Before covering the weldings of the lining according to step (b), it is preferable, according to the present invention, to mechanically treat the surfaces of the weldings and lining on which the above strips are to be placed, for example by grinding, to clean them and make them more uniform and without defects.

Step (c) of the present method is basically carried out analogously to step (b) above, with the difference that each strip (or plate) is not intended in this case to cover a welding of the lining, but is positioned on the surface of the lining, adjacent to at least one of the covering strips placed in accordance with step (b), and in the direction of at least one of the weep-holes, until the outlet on the surface of the lining itself is completely covered. In this way, by welding the edges according to the subsequent step (d), interstitial areas are formed communicating with this outlet and, directly or indirectly, with at least some of the interstitial areas formed near the original weldings of the lining. According to the method of the present invention, all the outlets of the weep-holes are covered with strips as described above, forming, by means of the underlying interstitial areas (or meati), obtained after the welding of step (d), intercommunicating passages from each point of the original weldings of the lining to at least one outlet of a weep-hole.

If one or more of the weep-hole outlets is applied through one of the original weldings of the lining, it is up to the operator to cover the outlet with the same strips used for covering the weldings, obviously without using any further strip according to step (c).

Also in step (c), it can be advantageous to carry out the different operations similarly to step (b). In particular, for example, to grind the supporting area of the strip to clean it and make it more uniform and without defects.

According to a preferred embodiment of the present method, in steps (b) and (c), a groove is produced in the surface of the lining or its weldings, underneath the covering strips. This groove normally has a width of between 5 and 20 mm, a depth of between 1 and 5 mm, selected on the basis of the thickness of the lining and the rheological properties of the process fluid. In particular, according to the present invention, the depth of this groove is preferably less than 30% of the thickness of the original lining.

This groove is preferably applied along all the original weldings of the lining, and in its surface when there is no welding, as in the case of the strips arranged in accordance with step (c). The groove has the function of facilitating the flow of the fluid coming from a possible loss of the weldings along the edges of the strips, making the detection of the loss more rapid and secure. The role of the groove near the junctions between two adjoining strips (or plates) is particularly advantageous.

Step (d) of the method of the present invention comprises the welding of the edges of the strips (or plates) shaped and arranged as described in steps (b) and (c). The welding method is not critical and any of the methods available in the known art can be used, provided it guarantees the production of corrosion-resistant weldings and mechanical properties suitable for the operating conditions of the equipment.

The welding is preferably carried out with arc electrodes or "T.I.G." with wire rods. The longitudinal edges are welded onto the surface of the underlying lining, and the adjoining edges of each pair of strips to each other. The latter can at the same time also be welded to the underlying lining. In this way, underneath, between the surface of each strip (or plate) and the surface of the lining near the original welding, there is an interstitial area (or meatus) suitable for the flow of a fluid during a possible loss.

According to the present invention, the welding of at least a part of the adjoining edges of the strips is carried out so that there remains an opening underneath the welding itself, so as to put the interstitial areas (or meati) in communication with the possible grooves existing under the strips by each side of the welding. This opening, or passage, under the welding between adjoining edges, must be hermetic in every point with respect to the internal chamber of the equipment, where the process fluid is present during normal operation.

According to the present invention the appearance and arrangement of these intercommunicating openings are not critical, provided they comply with the above demands and the arrangement is such that the openings, as a whole, in the case of a loss from the weldings of the strip edges, allow the process fluid to flow from any point of the above interstitial areas (or meati), until it reaches at least one of the weep-hole outlets. It is not necessary however for all the interstitial spaces (or areas) to be intercommunicating, as it is sufficient that there be communication, directly or indirectly through a sequence of openings and interstitial areas, with at least one of the weep-hole outlets. It is preferable, according to the present invention, for only from 50 to 80% of the weldings between adjoining edges to comprise an underlying intercommunication opening.

Depending on the way in which the adjoining strips and edges are arranged in steps (b) or (c), there are various solutions for the practical embodiment of the invention.

For example, if the adjoining edges of two strips have been partially superimposed (as schematically illustrated in FIGS. 4 and 6 enclosed), it is normally sufficient to weld all the external edges of the strips themselves to the underlying lining and to each other. The edge of the underlying strip, in the super-imposition area, remains on the inside and is not therefore welded, preventing the welding deposit from locally blocking the interstice (or groove) and thus ensuring the presence of an intercommunication opening.

According to another form of embodiment, in steps (b) and/or (c) (as already mentioned), a flat plate of the same material as the strips is placed under the junction between two adjoining strips, preferably in a cavity especially prepared in the original welding and/or lining, and the adjoining edges of these are placed over this, adjacent to each other.

This kind of arrangement of the elements corresponds to what is schematically illustrated in FIG. 3. The flat plate has a width and length which are such as to completely be completely covered by the strips, and a thickness normally of about 2–4 mm. The edges of the strips are then hermetically welded to each other (where adjoining) and to the underlying lining. The flat plate under the adjoining edges prevents a welding deposit from blocking the underlying interstitial area (or meatus or groove).

In a further embodiment, particularly preferred, two adjoining edges are placed adjacent to each other and only partly welded, leaving at least a part in the central area of the junction unwelded. This unwelded part, which forms a communicating opening between the interstitial spaces under each strip at the sides of the welding, is preferably between 5 and 30 mm long.

The unwelded parts are then covered by placing metal plates over them, suitable shaped and of the same anti-corrosive material as the strips and then hermetically welding the edges of these onto the underlying metal. This operation must be carried out in such a way as to guarantee the hermetic sealing of the total surface exposed to the process fluids of the equipment. Flat plates which are suitable for this embodiment of the present invention have adequate dimensions for covering the entire length of the interrupted parts and are preferably square or rectangular. The dimensions are preferably between 20 and 200 mm. The thickness of the plates is preferably between 4 and 25 mm.

Figure 2:
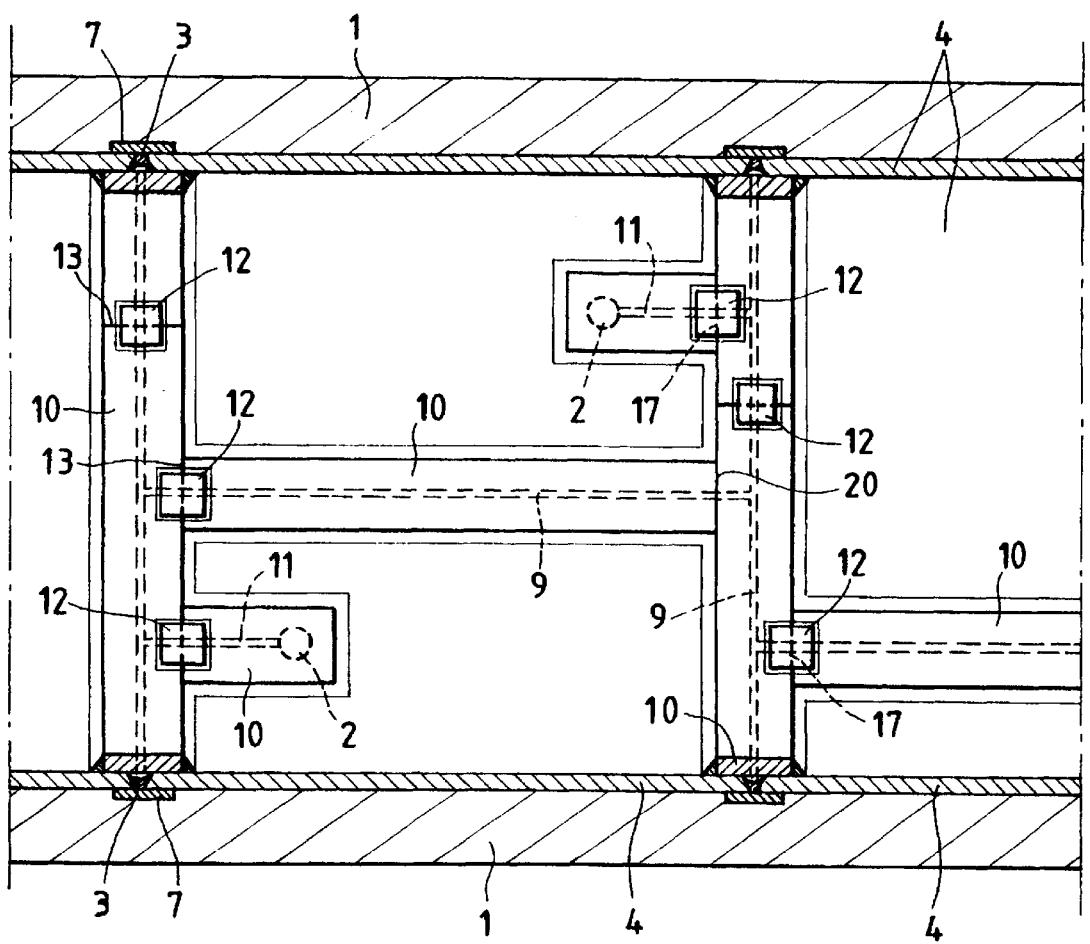

This latter embodiment of the present invention enables an arrangement of the essential elements to be obtained corresponding to that schematically illustrated in FIGS. 2 and 5.

Other forms of embodiment, such as, for example, those previously described in particular, in the application of the method to a single piece of equipment, are not excluded however from the scope of the present invention.

In the preferred case in which grooves are applied before the placing and welding of the strips as described above, these grooves, passing under the weldings between adjoining edges, form in themselves excellent communication openings.

According to a particular embodiment of the present invention, steps (a), (b), (c) and (d) can be carried out contemporaneously, in the sense that each of the above steps can operate independently in different areas of the equipment. For example, it can be advantageous, especially in equipment of large dimensions, to carry out the welding of the edges of the strips according to step (d) in a certain area in which the original weldings of the lining and weep-hole outlets have already been covered, whereas covering steps (b) and (c) are carried out in another area. However, in each part of the equipment the intervention according to the method of the present invention is obviously carried out with step (d) subsequent to steps (a), (b) and (c), and step (c) subsequent to step (a), whereas the operating order between steps (b) and (c) is not particularly critical.

The method of the present invention enables safety operations to be carried out on existing equipment which is either new or already operating in a chemical plant. The scope of the present invention also comprises however the application of this method during the assembly and construction of new equipment to improve its duration and safety.

One of the advantages of this method is the possibility of dimensioning the strips and flat plates and suitably shaping them so that they can be inserted through the single opening of the man-hole normally existing in each equipment. This can also involve the use of relatively small plates, sometimes with a length of a few tens of centimetres, but this does not jeopardize reaching the desired safety measures as, according to the present invention, no interstitial area produced under them after weldining, however small it may be, remains isolated from at least one weep-hole. At the end of the intervention of the present method, the protection of the original weldings of the lining is thus guaranteed together with the rapid and safe detection of a possible loss during operation, from any point of the covering strips and weldings thereon and without any necessity of applying new weep-holes with respect to the original ones, or in any case, in particular cases, applying only an insignificant number compared to the total amount.

In addition, the method of the present invention can be carried out, for the same reasons mentioned above, without removing any part of the equipment and without removing this from the operating site. The application and completion of the method are normally possible in fact within a week and can be carried out during a normal stoppage of the plant (also called shutdown) for its control.

The applicative characteristics of the method of the present invention are better illustrated by referring to the drawings and diagrams shown in the enclosed figures, wherein:

FIG. 1 schematically represents a sectional view of a wall of conventional equipment in contact with corrosive process fluids, for example a reactor for the synthesis of urea;

FIG. 2 schematically represents a front view of a part (internal side) of the longitudinal section of equipment to which the safety method of the present invention has been applied;

FIG. 3 schematically represents a detail (front view and longitudinal and transversal sections) of a part of the lining welding, after positioning the covering plate of the present invention, comprising a junction and welding between two adjacent parts of the flat plate;

FIG. 4 schematically represents a detail (front view and longitudinal and transversal sections) analogous to that of FIG. 3, wherein the junction between two parts of flat plate is according to a second embodiment of the present invention;

FIG. 5 schematically represents a detail (front view and section) of a piece of lining welding, after the safety intervention of the present invention, comprising the derivation point and junction with a weep-hole;

FIG. 6 schematically represents a detail (front view and section) analogous to that of FIG. 5, wherein the derivation and junction with the weep-hole are in accordance with a different embodiment of the present invention.

In the figures, corresponding parts have, for the sake of simplicity, identical reference numbers. In addition the different elements are not represented in scale with each other to provide a better illustration of the distinctive characteristics of the present invention. The different figures enclosed are illustrative of the present invention but do not limit its scope in any way.

The section represented in FIG. 1 shows the pressure-resistant body 1, normally made of common carbon steel, and the original lining 4 of the reactor, made of a corrosion-resistant material, which has a welding line 3, overlapping a flat plate or strip 7 of the same material as the lining, to avoid the welding itself being in direct contact with the steel of the pressure-resistant body. In contact with the surface beneath the lining is the weep-hole 2, comprising an internal lining 8, which communicates with the interstitial area created between the lining itself and the pressure-resistant body, represented by the line 5. A possible loss from the welding 3 follows the direction 6 indicated by the dashed line.

FIG. 2 shows again the pressure-resistant body 1, the original lining of the reactor 4 and the weldings 3 with the underlying flat plates 7. The communication grooves 9 and 11 are also schematically represented, applied respectively on the weldings of the pre-existing lining and along the communication lines with the existing weep-holes 2 extended through the lining itself. Above the grooves are the covering strips 10, welded in turn by the edges to the underlying lining, and extending as far as the weep-holes. In the parts 13 where two adjoining strips meet and are welded, are the flat plates 12 welded above the former strips, hermetically covering the non-welded parts 17, forming the communication openings between the grooves. It is also possible to see the junction 20 between two adjoining strips, completely welded and without a communication opening, which was not necessary as both the sides of the welding already communicated with at least one weep-hole.

FIG. 3 shows the front view (A) and longitudinal (B) and transveral (C) sectional views respectively along the lines Z1 and Z2. The elements corresponding to those already indicated in FIG. 2 have the same reference numbers. The welding detail 13 between two covering strips 10, which are adjoining, shows the groove 9 and the flat plate 14 underneath the welding 13, which is of the same material as the lining or of a different material provided this is corrosion-resistant and weldable to the lining. The function of the flat plate 14 is to prevent, at the moment of welding 13, the groove 9 from being filled with the welding deposit and the communication between the interstices beneath the two adjoining strips from being interrupted. To facilitate vision, the flat plate 7 beneath the welding 3 is not indicated in view (A).

FIG. 4 shows a front view (A) and longitudinal (B) and transversal (C) sectional views respectively along lines Z3 and Z4. The elements corresponding to those already indicated in FIG. 2 have the same reference number. The detail of the superimposition area 15 between two adjoining covering strips 10' and 10", shows the underlying groove 9, which makes the interstitial spaces or meati existing between these strips and the lining 4 intercommunicating. The weldings around the superimposition area make the interstitial spaces and the groove hermetic with respect to the process fluids. This arrangement prevents the transversal welding 16 in particular, applied between superimposed strips 10' and 10" from blocking the groove 9. Also in this case, as in FIG. 3, the flat plate 7 beneath the welding 3 is not shown in view (A).

FIG. 5 schematically represents a front view (A) and a section (B), along the line Z5, of an embodiment of the junction between two perpendicular adjoining strips, one of which is positioned to cover one of the weep-hole outlets. In particular strip 10 can be distinguished, which covers a groove 9 applied on a welding 3 of the lining 4. Near the weep-hole 2, there is a groove 11, in the lining, which joins 9. The flat plate 10''' welded by the edges to the underlying lining and welded to strip 10 along the joining line 13, is superimposed on the flat plate 10'''. In the central area of the joining line 13 there is an unwelded part 17 to ensure communication between the underlying grooves 9 and 11. This part 17 is in turn covered by the flat plate 12 whose edges are welded to the underlying strips 10 and 10''' to ensure hermetic sealing towards the process fluid.

FIG. 6 schematically represents a front view (A) and a section (B) along the line Z6 of a detail analogous to that of the previous FIG. 5, but in which the communication passage between grooves and interstitial spaces is different and in some aspects is analogous to the solution described in FIG. 4, which is however included in the scope of the present invention. In particular strip 10 can be distinguished, which covers a groove 9 applied on a welding 3 of the lining 4. Near the weep-hole 2, is groove 11, in the lining, which joins 9. The flat plate 10''', is superimposed on the groove 11, which is welded by the edges to the underlying lining, and superimposed on strip 10 starting from the joining line 13. The detail of the superimposition area 18 between the two covering strips 10 and 10''', shows that the underlying groove 11 is never in contact with weldings, particularly with welding 19, thus avoiding any possibility of blockage during the weldings, which are necessary for ensuring the hermetic sealing of the system towards the process fluid.

A further object of the present invention relates to pressure equipment with an improved degree of safety, which can be obtained with the method previously described, comprising an internal chamber suitable for containing process fluid, surrounded by a pressure-resistant body equipped with weep-holes, made of a material subject to corrosion by contact with said process fluid during operation, lined, internally, with an anti-corrosive lining consisting of several elements joined to each other by weldings, wherein, in said equipment, at least a part of the weep-holes is extended towards said lining until it reaches the internal chamber, and wherein said weldings of the lining and weep-hole outlets are completely covered with adjoining strips (or flat plates), of the same material as said lining or other corrosion-resistant material weldable thereto, which are seal-welded on the edges to said lining and to each other to avoid contact of said lining weldings and outlets with the process fluid during normal operation, and they form, in the underlying area, interstitial areas (or meati) which are hermetic with respect to the internal chamber, characterized in that the arrangement and weldings between the edges of at least a part of the adjoining strips, are effected so that, beneath each of the weldings between the adjoining edges, there is an opening between the existing interstitial areas (or meati) on each side of the welding, these openings being hermetic with respect to the internal chamber and in such a quantity and so arranged as to put each interstitial area (or meatus), or part of it, in communication with at least one of the weep-hole outlets.

Particular embodiments of the above equipment, which do not limit the scope of the present invention, comprise the particular arrangements of elements schematically shown in FIGS. 2 to 6 described above.

Following the above description of the present invention in its general characteristics and details, a practical applicative example is provided which should not be considered, however, as limiting the scope of the invention itself.

EXAMPLE

An intervention was carried out according to the method of the present invention, by isolation from the process fluid and application of a safety process of the weldings of the lining of a reactor of a plant for the production of 400 tons/day of urea.

This reactor operated at 160 bars and 190° C., with a reaction mixture comprising, under steady operating conditions, $NH_3$, $CO_2$, urea, water and air as passivating agent. The reactor basically comprised a vertical Vessel consisting of a cylindrical pressure-resistant body with a single wall (annealed, with a thickness of about 65 mm), having an internal diameter of 1.4 m and a length of 24 m, equipped with two forged hemispherical caps, of about the same thickness, placed at the upper and lower ends. On the upper end there was a circular man-hole, with a diameter of about 500 mm. The internal anticorrosive lining was made of ASIS 316L steel, urea grade, and consisted, in the central area of the reactor, of semicylindrical elements welded to each other, having average dimensions of 2.2×5.0 m and a thickness of about 10 mm. Near the outlets, caps and man-hole, the lining consisted of elements of smaller dimensions and with a more complex geometry. The surface expansion of the internal chamber of the reactor was about 110 m². In the pressure-resistance body there were a total of 20 weep-holes, each having a diameter of 20 mm, at an appropriate distance from each other. FIG. 1, described above, schematically represents a detail of the arrangement of the elements of this reactor, around a weep-hole near a welding of anticorrosive lining.

After testing the wholeness of the pressure-resistant body and ensuring that the weldings of the lining had no defects or losses, 15 of the existing weep-holes were extended through the lining until they reached the surface of the internal chamber, making sure the edges of each hole applied were welded to the lining itself, to avoid, in the case of a loss, infiltrations of the process fluid corroding the steel of the pressure-resistant body.

The supporting surface of the covering strips (or flat plates were then prepared by grinding both sides of the weldings of the lining. The same operation was carried out along the joining lines, previously marked on the surface of the lining, between the weep-hole outlets and at least one of the bordering weldings.

Intercommunicating grooves having a depth of about 1–1.5 mm, were then applied on the weldings, comprising those in the caps and around the outlets and man-hole, as well as on the joining lines as far as the weep-hole outlets. They were subsequently covered with plates made of 25/22/2Cr/Ni/Mo steel, having a width of about 100 mm and a thickness of 5 mm, adequately performed and adapted by pressure to the shape of the existing lining. The covering flat plates, most of which had a length of between 1 and 3 m, were contiguously arranged so as to completely cover all the grooves applied on the surface of the lining and the weep-hole outlets. To do this, the adjoining edges were adjacently arranged in contact with each other but without superimposing them. The edges of the flat plates were then seal-welded by electric arc to the underlying lining and to each other if adjoining, making sure, during the welding of the adjoining edges to each other, that an unwelded part having a length of about 20 mm was left, in the central area, in approximate correspondence with the underlying groove.

Some of the adjoining edges, however, were completely welded to each other and to the underlying lining, when no communication between the underlying grooves was necessary as each one already individually communicated with at least one weep-hole. This method of procedure, although optional, enables the network of grooves applied to the lining to be divided into a limited number of areas isolated from each other (in the example, 4–5 areas), each communicating with 2–4 weep-holes.

A plate of the same material as the flat plates, square-shaped and with a side of about 40–50 mm, was then placed on top of each of these unwelded parts to cover it completely. The thickness was about 5 mm. The edges of each plate were then seal-welded, onto the underlying adjoining plates.

At the end of the intervention, each of the grooves beneath the covering flat plates generally communicated with two or three weep-holes, without there being any necessity of applying any further weep-holes, with respect to those originally existing in the pressure-resistant body. The inside of the reactor thus modified (central area) corresponds to the diagram represented in FIG. 2, which indicates in particular the flat plates 10 placed over the grooves 9 and 11 applied respectively on the weldings 3 of the lining 4 and on the lining itself to allow communication with the weep-hole outlets 2. The adjacent edges of each pair of adjoining flat plates are only partially welded to each other along the joining lines 13, whereas the central part 17 is not welded and is covered, hermetically, by the plates 12. The edges 20, of a pair of adjoining flat plates, perpendicular to each other, are on the other hand completely welded to each other, without any communication between the grooves underneath each flat plate, as these are already communicating with at least one weep-hole.

FIG. 5 schematically shows a significant detail of the appearance of the reactor obtained according to the present invention, in the embodiment illustrated, relating to the assembly of the various elements in the communication area between a groove 9 applied on a welding 3 and the weep-hole 2, through the groove 11. In particular it is possible to see the partial welding of the adjoining plates 10 and 10''', and the interrupting part 17, covered by the plate 12.

At the end of the intervention the reactor was subjected to the usual tests to ensure it functioning. In particular the following tests were carried out:

Control of the welding with penetrating liquids according to "ASME VIII, div. 1, appendix 8";

Gas seal test according to "ASME V, article 10", carried out with helium;

Pressure seal test, carried out by bringing the internal pressure of the reactor to the value specified by the project specifications (200 bars).

All of the above tests gave satisfactory results.

What is claimed is:

1. A pressure container with an improved safety degree and life, comprising:
   a pressure-resistant body equipped with weep-holes and formed of a material subject to corrosion when contacted by a process liquid;
   an anti-corrosive lining made up of several elements welded to each other so as to line the inside of the pressure resistant body and define a chamber for containing the process fluid, and having a plurality of lining holes each corresponding to a weep hole forming outlets for a chamber defined by the lining;
   a plurality of first strips made of a corrosion-resistant material, pre-shaped to suitably lay on the surface of the lining near weldings of said elements and covering the weldings;
   a plurality of second strips of corrosion-resistant material each adjoining a first strip with an outlet such that all the outlets are covered;
   a plurality of strip welds joining the edges of said first and second strips onto the lining and adjoining strips,
   wherein each of said first and second strips are welded so as to form a hermetic channel with respect to the internal chamber and suitable for the flow of the process fluid, each channel being in communication with at least one of the outlets.

2. A pressure container according to claim 1, wherein said pressure container is configured to produce urea.

3. The pressure container according to claim 2, wherein said pressure container configured to produce urea comprises a reactor for one of a synthesis of urea, a condenser of carbamate, and a decomposition of carbamate.

4. The pressure container according to claim 1, wherein said pressure container is configured to withstand a pressure between 100 and 500 bars.

5. Method for increasing the safety of a pressure container comprising an internal chamber suitable for containing a process fluid, surrounded by a pressure-resistant body endowed with weep-holes and made of a material subject to corrosion by contact with said process fluid during running operation, said chamber coated inside with an anticorrosive lining made up of several elements welded to each other, by avoiding contact of said pressure-resistant body with the process fluid as a result of a possible loss from the weldings, said method comprising the following steps:

(a) extending of at least a part of the weep-holes through the lining to form an outlet in the internal surface of the container;

(b) covering the weldings with adjoining strips or flat plates of the same material as the lining, or other corrosion-resistant material weldable thereto, previously shaped to suitably lay on the surface of the lining near the weldings;

(c) placing on the outlets of the weep-holes further strips of the same material as the lining, or other corrosion-resistant material weldable thereto, each adjoining to at least one of the above strips of steps (b), until all said outlets are covered;

(d) hermetically welding the edges of each strip of steps (b) and (c) onto the lining and edges of other adjoining strips, to obtain, between each of these strips and the underlying surface of the lining and/or its weldings, a hermetic interstitial space with respect to the internal chamber and suitable for the flow of the process fluid;

wherein at least a part of the weldings between the adjoining edges of the adjoining strips are effected so that beneath any such welding there is an opening between the existing interstitial spaces on each side of the welding, said openings being hermetic with respect to the internal chamber and in such a number and so arranged as to put each interstitial space in communication with at least one of the weep-hole outlets.

6. The method according to claim 5, wherein said steps (a) through (d) are performed on a pressure container having a pressure-resistant body having a thickness of between 20 and 400 mm and made of carbon or low-alloy steel, and an anti-corrosive lining having a thickness of between 2 and 30 mm and comprising at least one of a metal, a metal alloy selected from titanium, zirconium, lead, vanadium, tantalum, and ASIS 316L steel (urea grade), INOX 25/2212Cr/Ni/Mo steel, and special austenitic-ferritic steels.

7. The method according to claim 5, wherein said steps (a) through (d) are performed on a pressure container having a pressure-resistant body comprising a single-wall annealed type.

8. The method according to claim 5, wherein step (a) comprises extending between 70 and 100% of the weep-holes of container as far as the chamber.

9. The method according to claim 5, wherein in steps (b) and (c) each are performed using strips having a width of between 50 and 300 mm, and a thickness of between 2 and 30 mm.

10. The method according to claim 5, further comprising, before steps (b) and/or (c) are performed, producing a groove along the surface of the lining, or along the weldings thereof, in the area subsequently covered by the first and/or second strips in order to form said channel.

11. The method according to claim 5, wherein said step of producing a groove comprises producing a groove having a width of between 5 and 20 mm, and a depth of between 1 and 5 mm.

12. The method according to claim 5, wherein said steps (b) and (c) each comprise arranging the adjoining edges of the first and strips on top of each other.

13. The method according to claim 5, wherein said steps (b) and (c) each comprise arranging the adjoining edges of the first and second strips adjacent to each other.

14. The method according to claim 5, wherein said steps (b) and (c) each further comprise:

partly welding adjacent adjoining edges, leaving an unwelded part between two ends of said strips, the unwelded part preferably having a length of between 5 and 30 mm; and subsequently covering the unwelded part with a plate of the same material as the strips; and hermetically welding the edges of the plate onto the underlying metal, so as to form said channel as a communication opening underneath each plate and adjoining edges.

15. The method according to claim 5, wherein said step of covering the unwelded part with a plate comprises covering the unwelded part with a plate having dimensions of between 20 and 200 mm and a thickness between 4 and 25 mm.

16. A pressure container according to claim 1, wherein said pressure-resistant body has a thickness of between 20 and 400 mm and is made of carbon or low-alloy steel, and said anti-corrosive lining has a thickness of between 2 and 30 mm and comprises one of a metal, a metal alloy selected from titanium, zirconium, lead, vanadium, tantalum, ASIS 316L steel (urea grade), and INOX 25/22/2Cr/Ni/Mo steel, and a special austenitic-ferritic steel.

17. A pressure container according to claim 1, wherein the pressure-resistant body is of the single-wall, annealed type.

18. A pressure container according to claim 1, wherein the first and second strips have a width of between 50 and 300 mm, and a thickness of between 2 and 30 mm.

19. A pressure container according to claim 1, further comprising a groove along the surface of the lining, or along the weldings thereof, in the area underlying the covering strips said groove forming part of said channel.

20. A pressure container according to claim 1, wherein the adjoining edges of the first and second strips are arranged adjacent to each other.

21. A pressure container according to claim 20, wherein the adjacent adjoining edges are only partly welded, leaving an unwelded part between two ends of the strips, preferably having a length of between 5 and 30 mm, the unwelded part is subsequently covered by a plate of the same material as the strips, and edges of the plate are hermetically welded onto the underlying metal, so as to form a said channel, underneath each plate and adjoining edges.

22. A pressure container according to claim 21, wherein the dimensions of the plate are between 20 and 200 mm and have a thickness of between 4 and 25 mm.

* * * * *